United States Patent [19]
John

[11] Patent Number: 6,016,444
[45] Date of Patent: *Jan. 18, 2000

[54] AUTOMATIC CONTROL OF ANESTHESIA USING QUANTITATIVE EEG

[75] Inventor: Erwin Roy John, Mamaroneck, N.Y.

[73] Assignee: New York University, New York, N.Y.

[*] Notice: This patent is subject to a terminal disclaimer.

[21] Appl. No.: 08/988,076

[22] Filed: Dec. 10, 1997

[51] Int. Cl.[7] .................................................... A61N 5/00
[52] U.S. Cl. ...................... 600/544; 600/545; 600/300; 604/65; 128/910
[58] Field of Search .................... 600/544, 545; 128/897–898, 910; 604/64–67

[56] References Cited

U.S. PATENT DOCUMENTS

| | | | |
|---|---|---|---|
| 4,533,346 | 8/1985 | Cosgrove, Jr. et al. | 604/66 |
| 5,230,344 | 7/1993 | Ozdamar et al. | 600/544 |
| 5,678,560 | 10/1997 | Sakamoto et al. | 600/545 |
| 5,699,808 | 12/1997 | John | 600/544 |
| 5,730,146 | 3/1998 | Itil et al. | 600/545 |
| 5,775,330 | 7/1998 | Kangas et al. | 128/731 |

*Primary Examiner*—Cary O'Connor
*Assistant Examiner*—Michael Astorino
*Attorney, Agent, or Firm*—Eliot S. Gerber

[57] ABSTRACT

A quantitative electroencephalograph (QEEG) based method and system for automatically controlling anesthesia is called a Closed Loop Anesthesia Controller (CLAC). An anesthetic is administered until the patient has attained the desired plane of anesthesia and a QEEG self-norm is then obtained. If the patient's brain waves exceed a confidence interval, centered at the set-point of the self-norm, the administration of the anesthesia is automatically adjusted.

31 Claims, 1 Drawing Sheet

AUTOMATIC CONTROL OF ANESTHESIA USING QUANTITATIVE EEG

FIELD OF THE INVENTION

The present invention relates to medical systems and methods and more particularly to an electroencephalograph (EEG) based system for automatic control of anesthesia during surgical operations, called a Closed Loop Anesthesia Controller (CLAC).

BACKGROUND OF THE INVENTION

At the present time anesthetics, drugs which induce loss of awareness, are often used for surgical operations. A general anesthetic should cause a progressive depression of the central nervous system and cause the patient to lose consciousness. In contrast, a local anesthetic will affect sensation at the region to which it is applied.

Generally the patient, prior to the surgical operation, is anesthetized by a specialized medical practitioner ("anesthesiologist") who administers one or more volatile liquids or gases, such as nitrous oxide, isoflurane, desflurane, ethylene, cyclopropane, ether, chloroform, halothane, etc. A preferred gas is Ciboflorane (TM Abbott) which, however, may sometimes not be used because of its cost. Alternatively, non-volatile drugs may be administered by injection or intravenous infusion, such drugs including pentothal, propofol, evipal and procaine.

The objectives of a correctly administered general anesthetic include:

(1) the patient's movements are blocked;
(2) the patient should feel no pain;
(3) the patient should be unaware of and not remember the operation;
(4) the anesthesia should not lower blood pressure to a dangerous extent (generally below 50 mm Hg for mean arterial pressure (MAP)).

A skilled anesthesiologist may monitor the vital signals (breathing, blood pressure, etc.) of the patient to determine if more, or less, anesthetic is required. Often he/she looks into the patient's eyes to determine the extent of the dilation of the pupils as an indication of the level (depth) of the effect of the anesthesia (called "plane of anesthesia"). However, there may be a number of problems with such complete reliance on the availability, skill and attention of the anesthesiologist. In some operations, such as some heart surgery, the head is covered so that the patient's eyes cannot be viewed. Some operations may be prolonged, for example, 10 to 15 hours, so the attention of the anesthesia nurse or anesthesiologist may flag or fail.

An anesthesiologist may not be available in some situations and localities. For example, in an emergency or battlefield situation, a general physician or surgeon may be present and able to perform an operation, but an anesthesiologist is not available. Similarly, in isolated geographic locations, especially in second- and third-world countries, it may be impractical to move the patient to a hospital center for an operation. A physician or surgeon would be able to perform the operation if there were some way to safely anesthetize the patient.

It has been suggested in prior patents that some of these problems would be avoided by having a computer system determine the best amount of anesthetic. However, such computer determinations have not been accepted and are not being used.

U.S. Pat. No. 2,690,178 to Bickford relates to an automatic system to apply anesthetics to a patient by monitoring the patient's brain waves. Bickford used the integrated potential output of the cortex. U.S. Pat. No. 4,280,494 to Cosgrove et al is entitled "System For Automatic Feedback-Controlled Administration of Drugs". It discloses a closed loop control of anesthetics, such as liquid thiopental, and the use of EEG electrodes. The EEG measure used is "EEG power response" ("total power output"). However, based upon present knowledge, it is believed that the use of the single measure of integrated cortex output or total power, as in Bickford and Cosgrove, does not a provide a reliable control signal for applying a general anesthetic. Many anesthetics actually cause an increase in power of the cortical EEG and, in some instances, the nature of power changes depending upon electrode position. Further, it must be emphasized that not only do different anesthetics have different effects upon the EEG, but those effects may vary from patient to patient as a consequence of different pre-medications and/or different biochemical sensitivities.

The inventor's prior U.S. Pat. No. 4,557,270, entitled "Electroencephalographic System For Intra-Operative Open-Heart Surgery", incorporated by reference herein, describes an electroencephalograph (EEG) system used intra-operatively in cardiovascular (open-heart) operations using a heart-lung machine (cardiopulmonary by-pass) such as heart valve replacement surgery. That system, called "CIMON" (Cardiovascular Intraoperative Monitor) is presently being sold by Cadwell Laboratories, Kennewick, Washington, and has been successfully used in many heart operations. However, the CIMON system, with its attention to cerebral ischemia related to the output volume of the heart pump, etc., is not used in general surgery and is not used to control the application of an anesthesia.

In Chamoun U.S. Pat. No. 5,010,891 EEG potentials from a group of healthy surgical patients are recorded (col. 14, lines 32–34). A "reference array" is obtained of the most significant locations and an "autobispectral density index" is defined based on the recordings from a normal group. Each normal group index is then compared to the index of the patient under review. However, the comparison of individual patients with a normal group, in itself, is not believed to provide reliable information in the surgical context of determining if a patient will be sufficiently anesthetized.

In Silberstein U.S. Pat. No. 4,869,264 light flash stimuli are given to a patient before and after the patient is subjected to a general anesthetic. The light flashes are at two or three frequencies and the patient's brain waves are detected by EEG. Silberstein mentions automatic control of an anesthetic but, for safety reasons, says that his system should be used to monitor patients.

SUMMARY OF THE INVENTION

In accordance with the present invention, a Closed Loop Anesthesia Controller (CLAC), including an EEG system and automatic quantitative analysis of the EEG (QEEG) is provided to apply the correct amount of anesthesia during an operation. Depending on the availability of an anesthesiologist, the system may permit a physician to automatically maintain the desired level of anesthesia in a patient.

General anesthetics produce a progressive depression of the central nervous system. Generally they produce an irregular descending paralysis of the central nervous system and suppression of the sensory cortex. The paralysis successively affects the basal ganglia, the cerebellum and the spinal cord; without suppression of the medula (respiratory, cardiac and vavometer functions). The sensory input to the cortex is suppressed because the sensory pathway from the brain stem reticular formation is inhibited. The nuclear reticulas inhibits the neurotransmitter gabaminobuteric acid which, in effect, closes the sensory gate to the cortex. The cells which normally regulate EEG on-going rhythm, generally in the center of the Alpha band, are cells of the nuclear reticulas, which are affected by the anesthetic to produce slower Alpha waves and Theta waves. These slower Alpha waves and Theta waves, and their distinction from the patient's normal EEG rhythm, are detected by the EEG system of the present invention and are used to automatically control the application of the anesthesia.

A set of EEG electrodes, preferably two or more, are removably fastened to the scalp of the patient. The physician or anesthesiologist will administer an anesthetic, preferably gas or an intravenous liquid, to the patient until the patient has attained the desired plane of anesthesia, in his clinical judgement, based upon the patient's vital signs and conventional clinical signs.

After the patient has attained the plane of anesthesia desired by the physician, the CLAC is activated to maintain that desired level. The patient's brain waves are detected and analyzed to form a self-norm ("reference") incorporating a set of QEEG features identified as sensitive to the depth of anesthesia. If the patient's brain waves during the operation remain within a confidence interval (band) close to the self-norm, the patient should remain at the same desired plane of anesthesia and additional anesthesia need not be given to the patient. Depending on the direction of movement of the analyzed brain waves, outside of the confidence interval, more or less anesthetic will automatically be administered.

The present invention presents a relatively simple and yet effective and reliable system and method for control of anesthesia. The method is based upon computation of the covariance matrix of spectral EEG features within each electrode and among a set of electrode positions. In its simplest form, it uses an anterior (frontal) EEG electrode and a posterior EEG electrode, which are preferably applied at the center line. A comparison is made of the absolute and relative EEG power within each of the two electrodes at selected frequency bands, preferably Theta and Alpha, and the relationships among these spectral measures within and between the set of electrodes. When the patient attains the surgical plane of anesthesia, the cross-spectral matrix will change; the power in each band will change within each electrode and, in addition, the anterior electrode may show greater relative increase in power in some bands than the posterior electrode. The mean and standard deviation of baseline samples or the covariance matrices and of these measures will be used to define a self-norm. If the patient starts to regain consciousness, these changes will begin to reverse. The confidence level around the self-norm (mean±2 standard deviations) will be exceeded. If that occurs, more anesthetic will automatically be delivered (titrated) to the patient. Conversely, if these changes are augmented, less anesthetic will be delivered. By constantly evaluating the momentary values in the covariance matrix relative to those defined by the self-norm, the system may reliably intervene to control the administration of anesthetic in a manner optimized for the individual patient.

This simple system is an application of the general concept of quantification of spectral power measures and their relationships within two (or more) EEG electrodes and evaluating change relative to a clinician-defined state. In addition, a more exact result may be obtained by using more EEG electrodes and more measures.

It has been found that the amount of absolute or relative brainwave power in the theta band (3.5–7.5 Hz) is inversely proportional to cerebral blood flow or metabolism. When brain activation decreases, these measures of brain wave power will increase, and vice versa, indicating that a suitable adjustment may be required. The EEG electrodes will detect increased theta power, reflecting diminution in the regions near the electrodes.

It has also been found that early components (brain stem), mid-latency components (thalamus-primary cortical response), and longer latency components (cortical response) of the auditory or somatosensory evoked response may be analyzed to provide an indication to the system of changes in the patient's ability to store implicit memories or to feel pain. The anesthesia prolongs transmission through the brainstem or thalamus. The likelihood of memory storage is preferably detected by measuring the latency and amplitude of mid-latency and later components of the AER (Auditory Evoked Response), while pain sensitivity is reflected by the SER cortical components of the SER (Somatosensory Evoked Response).

The "latency" is the time period following the presentation of a stimulus until a particular component occurs. The interval between successive EP (Evoked Potential) components is especially reliable as an indicator of brainstem state. For example, the interval between Peak I, arising from the arrival at the brainstem of an incoming stimulus via the auditory nerve, and Peak V, arising from arrival of that information at the inferior colliculus nucleus in the diencephalon, in normal persons older than 1 year, is approximately 4.0±0.2 milliseconds, which represents the time required for normal transmission through the brainstem.

The system provides a timed sequence of concurrent stimulations, in one or two sensory modalities (modes), to the patient. Preferably, stimulations are used in two different modes, such as an audio tone or click at one repetition rate (F1) and electrical shocks to peripheral nerves at a second repetition rate (F2). The stimuli, although concurrent, are at different prime number frequencies to permit separation of different EPs and avoid interference. Such concurrent stimulations or EP permit a more rapid, and less costly, examination and provide the patient's responses more quickly. Based on the responses to these multimodal stimulations, the CLAC system tests the functional state of the spinal cord (SER—Somatosensory Evoked Response) and brain stem (Brain Stem Auditory Evoked Response—BAER).

Before the operation, the anesthesiologist will removably attach two to eight EEG scalp electrodes to the patient. If eight active electrodes are used, they are placed over the six main brain arteries, namely, left and right frontal, left and right center and left and right back and the "watershed" region" on each hemisphere. Reference electrodes may be on the vertex, linked earlobes or mastoids and a ground lead should be on the forehead. He/she will then administer the selected anesthesia to place the patient in the desired plane of anesthesia. At that time, measurements are made of the patient's EEG, AER and/or SER to provide an adequate self-norm (reference or base line). Measures of vital functions such as heart rate, EKG waveshape, R-R interval, blood pressure, respiration and temperature may also be obtained and monitored.

In theory, the EEG system, which monitors the electrophysiology of the patient, should detect changes in the clinical state, i.e., changes in the depth of anesthesia, probability of memory storage (remembering the operation) or sensitivity to pain, before there are clinical or qualitative signs of change, such as movement, tachycardia, or increased blood pressure. During the operation, the EEG system automatically and continually collects on-going EEG and also challenges the patient with regularly repeated periods of stimuli to provide evoked potentials, such as AER and SER. These data are subjected to automatic artifact removal and features selected from the self-norm are continuously analyzed, displayed as a trajectory, and deviations beyond the confidence limits (reference band) established by the self-norm are used to automatically control the application of anesthesia.

The servo control is optimized in the present invention (CLAC) by automatically calculating a system "transfer function" for each patient at each operation. That transfer function is not based on population statistics (normal group) relating to a particular anesthetic and type of operation because of the unique biochemical reactions of each patient. The transfer function is a quantitative measure of the particular patient, at the time of the operation, to the particular anesthetic and will be used by CLAC to control the application of anesthetic during the patient's operation. The preferred method to calculate the transfer function uses perturbation analysis. After the patient is anesthetized to the desired plane of anesthesia, and his QEEG self-norm (reference set-point) is obtained, the system (CLAC system) halts delivery of the anesthetic, or may diminish the delivered amount by some fraction, for example, 50%. The patient will then start, in a gradual way, to arise out of the specified plane of anesthesia. At a small statistically significant or selected distance from the set point, preferably about 2.5 Standard Deviations (S.D.), i.e., about 1%, the application of the anesthetic is resumed. The CLAC system, by this process, will determine how many units of anesthetic were withheld from the patient to cause the level of anesthesia to rise to the selected level. For example, it may require withholding 8 units for the patient to be roused to 2.5 S.D. from the set-point. The amount of anesthetic withheld, called the "test correction amount", is an approximation of the amount of anesthetic required to restore that particular patient to the plane of anesthesia when he deviated from his set point by 2.5 S.D. A selected fraction of that amount is automatically administered by the CLAC system, as a first approximation, to test if the patient is restored to the set point. The amount required to restore the patient to the set point is the "correction amount" and is retained in system memory and is administered to the patient whenever the patient deviates from his set-point by 2.5 S.D.

Because anesthetic agents are distributed within several body compartments in a manner which changes with the duration of anesthesia, and because such accumulations may be released to the brain as distribution coefficients change, adaptation to such changing pharmacokinetics requires that the correction unit be re-confirmed at regular intervals, for example, every 15 minutes. Further, adequate determination of the transfer function may require positive as well as negative perturbations, that is, periodic evaluation as above of the increased depth of anesthesia caused by a small increment in the amount of anesthetic delivery, for example 10%, until a statistically significant increase of level is noted.

We presently assume a linear relationship so that a proportional amount of anesthesia is administered for greater deviations of the patient from his set-point, should that occur.

DETAILED DESCRIPTION OF THE INVENTION

Figures 1, 2, 3:
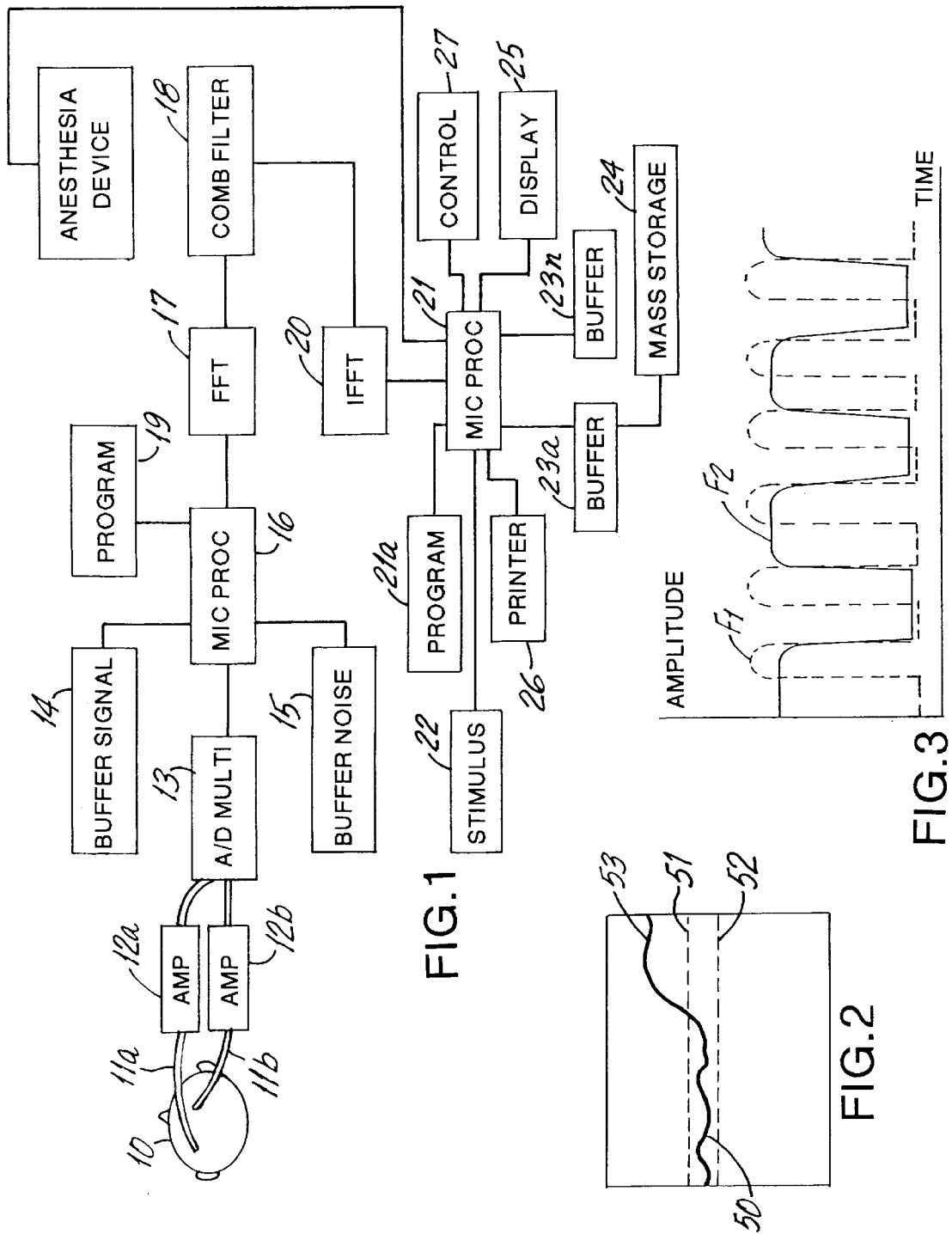
FIG. 1 is a block schematic drawing of the apparatus of the present invention.
FIG. 2 is a chart showing a QEEG trajectory.
FIG. 3 is a chart showing the timing of two stimulations, for example, auditory clicks and somatosensory skin voltage pulses, which are simultaneous and out-of-phase.

As shown in FIG. 1, prior to a surgical operation, preferably two EEG electrodes 11a and 11b are removably secured to the scalp 10 of the patient. Preferably only two EEG electrodes are used which are anterior (front center $F_Z$) and posterior (back center $P_Z$). Alternatively six, or more, EEG electrodes are used, which should include the following locations: front left ($F_3$), front right ($F_4$), center left ($C_3$), center right ($C_4$), back left ($P_3$) and back right ($P_4$). The capital letters F,C,P refer to position location names in the International 10/20 Electrode Placement System. In addition, reference electrodes are linked and are removably positioned on the patient's mastoids, or other suitable location such as a vertex ($C_Z$) to use as a reference for monopolar recording. Such a reference electrode may be used regardless of the number of EEG electrodes. A conventional EKG (electrocardiogram) electrode, may be placed on the shoulder or chest. A ground connection is placed on the forehead.

The electrodes preferably use a standard electrolyte gel, or other application method, for contact so that the impedances of each electrode-skin contact is below 5000 ohms. The EEG system, described below, checks the electrode-skin impedance at each electrode at frequent intervals, such as every minute, and displays a warning, such as a red LED light, if any such impedance falls below 5000 ohms.

As shown in FIG. 1, the patient's head 10 is connected with the desired number of active electrodes 11a–11b, preferably silver-silver chloride disk electrodes or less preferably needle electrodes. The drawing shows two active electrodes. When surgical conditions restrict access to some regions of the head, active electrodes may be located on the forehead and at the vertex or on the forehead with a reference electrode on either mastoid.

The electrodes 11a–11b are connected to respective amplifiers 12a and 12b, each electrode lead being connected to its respective amplifier. Each amplifier 12a–12b has an input isolation switch, such as a photo-diode and LED coupler, to prevent current leakage to the patient. The amplifiers 12a–12b area high-gain low-noise amplifiers for the EEG, preferably having a frequency range of 0.5 to 100 Hz, gain of 10,000 common mode rejection of 100 dB and noise of less than 1 microvolt peak-to-peak. For the brainstem auditory or somatosensory evoked responses the amplifiers have a frequency range of 30 to 1500 Hz, gain of 100000, common mode rejection of at least 100 dB, and noise less than one microvolt p-p. Amplifier parameters may be switched for separate data collection of EEG and EP, separate amplifiers may be connected to the same electrode input, or a programmable A/D multiplexer converter 13 may be used to output the separated data.

The amplifiers 12a–12b are connected to an analog-to-digital multiplexer 13 (A/D multiplexer). The multiplexer 13 samples the amplified analog brain waves at a rate compatible with the bandwidth of the amplifiers or is programmed to provide EEG and BAER/BSER outputs samples at the appropriate different rates. The multiplexer 13 provides, at its output, sets of digital data, representing the EEG and EP input analog signals. The multiplexer 13 is connected to "buffer signal" 14, which stores the signal, and "buffer noise" 15, which stores samples of the "noise", that is, amplifier output of EEG when no stimuli are delivered to elicit EPs. The buffers 14,15 and A/D multiplexer 13 are connected to the dedicated computer microprocessor 16. For example, the microprocessor may be an Intel 486 (TM) or Intel "Pentium" (TM) or a digital signal processor, such as the TM5320C32. The microprocessor 16 is connected, through its dedicated 512-point FFT 17 (Fast Fourier Transform) to digital comb filter 18 and is controlled by software program 19.

The comb filter is connected to, and controls, the IFFT 20 (Inverse Fast Fourier Transform). The output of IFFT 20 is connected to the system microprocessor 21, for example, Intel "Pentium" (TM). The microprocessor 21 is connected to, and controls, the stimulus devices 22 (lights, loudspeaker, shock device, etc.), the system digital storage buffers 23a–23n (only two being shown), the mass storage 24, such as a hard disk, the display 25, such as a CRT, and a print-out printer 26 and keyboard control panel 27. The microprocessor 21 operates under control of software program 21a.

The digital comb filter 18 may be as described in U.S. Pat. No. 4,705,049, incorporated by reference herein. The comb filter may be considered a series of band pass and band stop filters which are responsive over a selected range. The selected range is 0–1400 Hz and preferably there are band pass filters at 10–580 Hz, 600–640 Hz, 720–800 Hz and 900–1400 Hz and band-stop filters at 0–10 Hz, 580–600 Hz, 640–720 Hz, 800–900 Hz and above 1400 Hz. The band pass filters are the "teeth" of the comb which are selected so as to accord with the frequencies in which the signal/noise ratio is acceptable. The band-stop filters are selected to be at frequencies in which the noise is excessive.

The multiplexer 13 is programmed to obtain samples of the signal and of the noise. The "noise" is preferably obtained when there is an absence of evoked potential stimuli and the "signal" is obtained during stimulation, beginning with presentation of the stimuli or after a pre-selected delay.

The program 19 with its controlled microprocessor 16 condition the input signals and insure that they are valid biological signals. Such validation checks on the input signals include periodic calibration measurement and impedance measurements and continuous automatic artifact rejection algorithms.

The microprocessor 21 automatically provides a timed set of stimuli from stimulator 22 which may be an audio sound from a speaker or earphones, a visual signal from a light flash, or a tactile signal from an electric shock or a vibrator. Visual flashes may be delivered using LED goggles flashing at a rate of 1/second (VEP). Auditory clicks, about 100 db SPL, may be delivered through a stethoscope earpiece by air conduction tubes from a magnetic speaker. The rate of stimulus is preferably 7–50/second and most preferably 35–45/second, i.e., eliciting a 40 Hz auditory steady-state evoked response (40 Hz). Regular audio clicks and rare visual flashes or tactile stimuli may be combined into a randomly mixed stimulus sequence, with the EP elicited by the rare stimulus providing the cognitive "event-related potential", P300 (P3). The patient's brain will respond to these stimuli, providing "Evoked Potentials" (EP) which are averaged to reduce noise, providing an "Average Evoked Potential" (AEP). Sample size varies with stimulus mobility, ranging from 100 (VEP) to 512–2048 (BAER/BSER).

The AEP is the sum of samples time-locked to the onset of the stimuli divided by the number of samples, to provide an updated average.

When conditions permit, a full sample of these data will be obtained from the patient before induction of anesthesia, to facilitate subsequent computation of transfer functions relative to this "pre-induction baseline". If this is not feasible, the initial computations described below will be slightly (about 10 minutes) delayed.

The anesthesiologist, physician or other operator then administers the selected anesthetic to cause the patient to attain the selected plane of anesthesia, as determined by his clinical criteria. That determination is made by viewing the patient's blood pressure, respiration, eye pupil dilation, lash reflexes and other clinical signals. This level is referred to as the "set point".

The operator, who may be the anesthesiologist, physician or other operator, after the patient is at the set-point, instructs CLAC to collect a set of artifact-free EEG and AER and SER samples in the "set point self-norm" session. The data acquisition is automatic and the computer removes or excludes artifacts, by regression or other techniques. Preferably this self-norm session contains 60 seconds of EEG as well as EPs averaged using 2048 stimuli. The EEG system then subjects the data to spectral analysis using very narrow band (about 0.5 Hz steps) FFT (Fast Fourier Transform) and EP peak detection. Mean values and standard deviations across 24 2.5 sec epochs (S.D.) are obtained for absolute ($uv^2$) and relative (%) power in the Delta (1.5–3.5 Hz), Theta (3.5–7.5 Hz), Alpha 1 (7.5–10 Hz) Alpha 2 (10–12.5 Hz), Beta 1 (12.5–25 Hz) and Beta 2 (25–50 Hz) frequency bands. Alternative measures may be obtained by computing sensitive indices such as $$\frac{\text{delta plus theta}}{\text{alpha plus beta}} \quad \text{or} \quad \frac{\text{theta}}{\text{alpha}}$$

and calculating the ratio of such combined variables or of univariate measures of successive samples of EEG/EP relative to baseline values. An alternative to the Z-transform is to use the F-ratio derived from the variance within the samples divided by the variance of the baseline. Statistically significant thresholds can be defined for each of these alternatives. The covariance matrix is computed for these bands across the full set of electrodes for every such epoch and the self-norm average covariance matrix is calculated. Coherence and voltage gradients are also determined between each electrode and every other electrode separately for each band and for the total signal. The PI–PV latency interval for the BAER, the dorsal column nucleus (PA) to somatosensory cortex (PV) latency interval for the BSER (central conduction time—"CCT") are computed. The power in FFT at F1 and F2 is computed and used to provide an indicator of the arrival of auditory stimuli (F1) or somatosensory stimuli (F2) at the cortex.

The brain stem auditory evoked response (BAER) has, in normal subjects, 5 peaks. These latencies are expressed as milliseconds from the stimuli and are closely similar in shape and latency across neurologically normal persons. The time shift of certain of these latencies, and their suppression, is proportional to the patient's response to anesthesia. The first 5 positive peaks, in response to click (auditory) stimulus, are believed to reflect the successive activation of the acoustic nerve, cochlear nucleus, superior olivary complex, lateral lemniscus and inferior colliculus. The Peak I–Peak V latency interval is probably the preferred BAER indicator to use. The mid-latency (MLAER) responses at about 25 and 50 ms represent the response of the auditory cortex to incoming information and should be assessed with the 40 Hz SSER.

If the auditory stimulus is 40 clicks/sec. and an average EP is computed using an analysis epoch of 100 ms, the steady state evoked response (SSER) will reflect the arrival of auditory information to the cortex. The sum of the square root of the absolute difference between every two successive time points of the SSER across the 100 ms window is called the auditory response index (ARI) and provides an estimate of the likelihood that intraoperative auditory events such as conversations or comments by the surgical team might enter awareness of implicit memory storage. The ARI is a desirable element in the set of EP features.

Another useful indication of the patient's state is the brain stem somatosensory evoked response (BSER). It is believed that the successive peak latencies reflect, in order, the activation of the dorsal column nuclei, medial lemniscus, thalamus, sensory radiation and the first cortical synapses (P25 and P45). The PA–PI latency (CCT) is probably a good BSER indicator to use, and the amplitude and latency of the cortical responses of nominal P25 and P45 reflects the reception of stimuli at the cortex from pathways mediating the sensation of pain.

The feature extraction method for cortical evoked potentials involves alternative ways to describe EP signal strength, variability and interhemispheric symmetry. These features are extracted for latency domains: 80–140, 140–200 and 200–500 msec. Measures of signal strength ("features") include absolute peak-to-peak (p—p) amplitude and "normalized" p—p amplitude. Normalized p—p amplitude is obtained by defining the largest amplitude as 100%, and other measurements are scaled relative to that maximum. Measures of EP variability include the standard deviation of the p—p amplitude (s), the variance ($s^2$), and log variance (log $s^2$). The standard deviation of the p—p amplitude (s) is an rms measure: rms=$(^sPmax)^2-(^sPmin)^2$, where s is the standard deviation, and $_{Pmax}$ and $_{Pmin}$ are the largest positive and largest negative peaks, respectively, within a particular latency domain (100–250 msec or 250–500 msec). Log $s^2$ is computed because $s^2$ itself is not normally distributed. A measure of signal-to-noise ratio (S/N) is computed as well, where "signal" is the p—p amplitude, and "noise" is its standard deviation. The principal measure of bilateral EP symmetry is the Pearson product-moment correlation (r) across the time bins, computed for EPs recorded, when using six or more electrodes, from homologous derivations in left and right hemispheres ($C_3$ vs. $C_4$, $F_3$ vs. $F_4$ and $P_3$ vs. $P_4$, etc.), and referred to as "interhemispheric coherence." The square of the product-moment correlation coefficient ($r^2$) is also obtained for each homologous pair of derivations. Across a set of six electrodes, there are thus a large set of quantitative EEG descriptors, cortical EP descriptors, and brainstem EP descriptors. All of these various features are regularly updated, included in the covariance matrices to be compared against the self-norm.

Every measure may be z-transformed to rescale it, using the corresponding mean and standard deviation obtained from the baseline. Each Z-score is calculated in the following manner: the self-norm mean, X, for a particular measure, is subtracted from the value X for that measure obtained from the patient during the operation. The difference X–X is divided by the standard deviation, SD, of that measure in the self-norm. Thus, z=(X–X)/SD. If the distribution of a variable is Gaussian, the z-score provides an estimate of the probability that an observed measure is "abnormal", i.e., improbable.

In addition, a patient's measures are statistically compared with a normative reference database based on measures obtained inter-operatively from a group of normal patients of the same age having successful outcomes of specific surgical procedures using specific anesthetic materials. For example, a database is obtained on the surgical procedure of a prostate operation in a normal group of patients of the same age using the gas halothane. Further, the patient's measures are statistically compared to a normative reference database based on measures taken from a normal group having post-operative reports of successful operative administration of anesthesia, regardless of the operative procedure.

As EEG power at a given frequency equals the variance at that frequency, the ratios of power responsive to a first mode, i.e., auditory stimulation F1 (on/off) and a second mode, i.e., somatosensory stimulation F2 (off/on) are calculated. F1 and F2 are simultaneous but out of phase as shown in FIG. 3. Alternatively, auditory stimuli at F1 and tactile stimuli at F2 are continuous, providing a steady state response. 10-second samples of EEG are collected, FFT computed at 0.1 Hz increments and an average of N samples of the FFT computed. The power in the F1 and F2 windows (Fstim) and the average power in the windows, for example, 40 bins (B) above and below each of the stimulation frequencies, Fav, is used to compute the value of $$F2, B = \frac{Power\ Fstim}{Power\ Fav}.$$

These ratios, treated as F-values, provide statistical probability that the auditory stimuli are traversing the brainstem and the somatosensory stimuli are traversing the spinal cord and brainstem to reach the cerebral cortex. In addition, using trigger pulses at the F1 and F2 frequencies, the microprocessor computes the averaged brainstem auditory evoked responses (BAER), 40 Hz SSER, and somatosensory evoked responses (BSER).

At regular intervals (approximately 30 seconds) after the self-norm (baseline) is established, during the operation and also upon operator demand, a statistically adequate EEG and EP sample is automatically acquired and statistically compared to the set-point self-norm. Such comparison may be by computing the distance between the self-norm average covariance matrix and the covariance matrix of each updated sample or to a vector combination of Z-scores from univariate EEG/EP descriptors, and any significant deviation automatically activates the anesthesia supply system. For example, any deviation of the patient from his self-norm by ±2.5 S.D. causes an increase, or decrease, in anesthetic delivery.

It has been determined that a relatively simple and rapid analysis of only a few measures at only a few EEG electrodes provides a reliable method to control the application of anesthesia. This relies on a co-variant comparison between pairs of EEG electrodes. The preferred pair is one anterior electrode (front of scalp) and one posterior electrode (back of scalp) on the mid-line. An alternative preferred set would consist of 3 pairs of homologous electrodes on bilateral frontal, central and parietal positions.

One preferred measure is EEG power in the selected bands of Alpha 1, Alpha 2, Theta and Delta, and most preferably Alpha 1 and Theta. For example, power in the Alpha 1 or Theta band is compared as between an anterior and a posterior electrode. Another preferred measure would be the frequency which is below 95% of the spectral power, known as Spectral Edge 95, or SEF95, or below 50% of the power, SEF50. A comparison of EEG power in the selected measure at these electrodes defines a gradient from front to back. With the application of anesthesia the EEG output, in the selected bands, rises differentially at the anterior electrodes and the gradient changes. If that gradient decreases by more than a selected amount, for example, 10% of the selected measure, the patient is tending to be aroused and more anesthetic should be applied.

In addition to the collection and analysis of on-going EEG, discussed above, the patient is automatically subjected by the system of FIG. 1 to suitable stimuli at selected intervals over the course of operation to provide sets of auditory and somatosensory EPs (Evoked Potentials). Numerous quantitative EP descriptors are also extracted and Z-transformed.

The preferred method and system to compare the patient's EEG and EP measures with a normative reference data base is to use "discriminant functions" based upon distances. As mentioned above, the Z-scores are obtained for each feature, or the covariance matrix is computed across all features and all leads, and multivariate distances from the set-point are computed and are then used to distinguish between conditions (states) of anesthesia, for example, as follows:

(a) fully anesthetized—the patient's movements are blocked, the patient feels no pain and is not aware of the operation.

This is the desired condition.

(b) partially anesthetized—the patient's movements are not fully blocked or the patient feels some pain or the patient is at least partly aware of the operation. This condition is generally unsatisfactory.

(c) unanesthetized—the patient's movements are not blocked; the patient feels pain and is aware of the operation.

These conditions, or similar condition categories, of a patient during an operation, may be distinguished through discriminant analysis using discriminant functions. Such functions are composed of weighted combinations of subsets of variables, the subsets being age-related Z scores. Each of the subsets (each Z score) is selected, on the basis of experience and experimentation, because it significantly contributes to the discrimination, i.e., discrimination between fully anesthetized and partially anesthetized. The weighting of the subsets (how much should each Z score contribute toward the discrimination) is also based on experience and experimentation.

The distributions of features of two groups of subjects (where the groups belong to different diagnostic categories) can be thought of as two clouds of points in a multidimensional space in which each dimension corresponds to a feature. In this case, each feature is a Z score and the diagnostic categories are the degrees of anesthization. There may be no significant differences between two groups (i.e., between fully and partially anesthetized) in some dimensions (i.e., in some features) but there may be significant differences in other dimensions. A problem arises when these clouds of points overlap (i.e., when there is no apparent significant difference between the two groups with respect to some features). One attempts to define a boundary through the clouds of points to create a first zone which includes as much as practicable of the first group, and as little as possible of the second group, and a second zone which includes as much as practicable for the second group and as little as practicable of the first group. A third zone is defined to encompass an overlap region where no reliable classification can be made. In principle, a discriminant function weights the values of selected features for a new individual and adds these weighted values to specify a single point in the relevant multidimensional space. This single point then would be in one of the three zones, and the individual would be classified accordingly.

A use of discriminant analysis in QEEG is found in U.S. Pat. No. 5,083,571 relating to psychiatric classification of individuals, incorporated by reference. The present use of discriminant functions is not to classify a group into a class or an individual with respect to specific disorders (psychiatric diagnosis); but rather to characterize the brain state of a patient at a particular time (intraoperatively).

For this purpose, it is preferred that the discriminant analysis be performed, during the operation, using Z scores based on self-norms (the same patient pre-operation) and population groups (patients of the same age during similar operations using the same anesthetic).

A probabilistic classification of the anesthetized state of a patient can be determined using discriminant functions derived from stepwise discriminant analysis using data of the same patient prior to the operation or/and preoperative data from groups of patients. Each discrimination is based on n functions where n is equal to the number of states n that discrimination. The functions are defined as the sum of selected Neurometric variables, each multiplies by a coefficient. The selection of the variables and the weightings of the coefficients are matters of experience and experimentation. Generally, each variable is a Z score. The result of each function is a single discriminant score $s_i$. A classification probability $P_i$ that a patient's state belongs to group i; where i is for example fully, partially or not anesthetized, is calculated according to the following formula:

$$P_i = \frac{\exp(s_i)}{\sum_{i=i}^{n} \exp(s_i)}$$

The group (state, i.e., fully anesthetized) for which a patient has the highest probability $P_i$ is selected as a potential classification group (state).

This probability $P_i$ is then compared to a guardband cutoff level for this group $a_i$, $a'_i$, $a''_i$, . . . , where $a_i < a'_i < a''_i$, . . . which correspond to classification errors $\epsilon_i$, $\epsilon_i'$ and $\epsilon_i''$, where $\epsilon_i < \epsilon_i' < \epsilon_i$. For example, $\epsilon_i = 10\%$, $\epsilon_i' = 5\%$, and $\epsilon_i = 2.5\%$.

If $P_i < a_i$ then the patient is not classified. If $a_i < P_i a'_i$ then the patient is classified in group i, with confidences $1 - \epsilon_i$. If $a'_i \leq P_i < a''_i$ then the patient is classified in group i, with confidence $1 - \epsilon_i$. If $a''_i \leq P_i$ then the individual is classified in group i, with confidence $1 - \epsilon_i$.

The system will combine selected measures scaled relative to the baseline, and compute the combinations as "trajectories". Upper and lower control signal limits can be separately adjusted.

As shown in FIG. 2, the baseline is defined as a mean 50. The upper and lower confidence intervals of 2.5 standard deviations from the mean are shown as lines 51 and 52. Any excursion of the trajectory 53 beyond the confidence limit, defined by lines 51 and 52, is "abnormal" and will trigger a control signal.

During the surgical operation, the patient is kept on the EEG system of FIG. 1, or re-connected to the system if for some reason there is an interruption. Based on the QEEG trajectory, explained below, the microprocessor controls the anesthesia delivery device 40 (which may be a valve on a gas supply or a syringe on an intravenous infusion device) to increase, maintain constant or decrease the amount of anesthetic delivered to the patient.

The objective of the EEG monitoring is to provide the closed-loop system with sufficient information regarding the state of the patient's brain to control the application of that amount of anesthetic required to maintain the patient at the selected plane of anesthesia.

The periodic collection of artifact-free on-going EEG sessions and evoked potential changes, such as BAER/BSER, continues as long as the operation lasts. The data is collected, analyzed and features extracted from that data are evaluated relative to the self-norm, that is, the preinduction or the postinduction but pre-operative state of the patient.

Using the full set of EEG and EP features extracted from each electrode, as specified above, which define the self-norm, a covariance matrix is compute for each electrode versus every other electrode. This covariance matrix is continuously recomputed, updating with each successive EEG and EP sample. Multivariate statistical measures are used to define the "distance" in the signal space between each updated matrix and the self-norm obtained initially. The task of CLAC is to monitor this distance continuously and to administer anesthetic automatically to correct any deviation from the initial set point, as defined above, acting as a servo system to regulate depth of anesthesia by using the distance measure.

CCAC is a adaptive servo system. However, as a servo system it does not present the difficult problem of homing (oscillation about a new position) as its set-point is not an exact point. Instead, the set-point is within a guard band (confidence interval) which may be, for example, of ±2.5 SD.

The CCAC automatically calculates a "transfer function" and a "correction amount" for each individual patient, at each operation, using perturbation analysis. That calculation is based on a test of the patient after he has attained the desired plane of anesthesia and after his set-point has been calculated. The CCAC system then withholds anesthesia to bring the patient away from the set-point-by a selected distance, i.e., 2.5 SD. The application of the anesthetic is then renewed to bring the patient back to the set-point. The amount of anesthesia required to bring the patient back to the set-point (within the band) is the correction amount. The amount of anesthetic determined to constitute the correction amount will be administered automatically by the CCAC whenever the patient's distance measure deviates 2.5 SD from the set point. For example, the withheld amount of anesthesia may be 1 cc per minute, but the "correction amount" may be greater, i.e., 2 cc per minute. The 2.5 SD is an example of a small perturbation, but further experience may indicate that the criteria (2.5 SD) should be raised or lowered.

As discussed above, for complete specification of the transfer function it may be desirable to examine both positive as well as negative perturbations, i.e., augmenting as well as withholding anesthetic delivery until the criterion is exceeded to indicate a statistically significant increase in depth of anesthesia.

If the operation is prolonged, for example, over 20 minutes, the correction amount is recalculated on a periodic basis, for example, every 15 minutes. This avoids the possibility that the correction amount may be insufficient, or excessive, because the anesthetic taken into portions of the body, such as fat and muscle, may be discharged into the bloodstream during a prolonged operation.

The CLAC may separately determine, based on EEG measures, the probability of the patient's arising from the plane of anesthesia (Ex1) and the probability that the patient is unconscious (Ex2). These may be expressed and combined by the formula:

$$\frac{Ex1}{Ex1 = +Ex2} + \frac{Ex2}{Ex1 = +Ex2} = T(\text{total}).$$

If T is within a selected range, the patient may be considered within the guardband of his plane of anesthesia. For example, if his set point T is 0.45, his guardband may be set at 0.40 to 0.50.

In addition to the EEG electrodes an EMG (electromyograph) electrode may be used at a frontal scalp location. In effect, the EEG electrodes at the front of the scalp, when they detect energy in the Beta 2 band, are detecting muscle activity (acting as an EMG electrode). The operator can determine, in order to arrive at a proper plane of anesthesia, using the frontal electrodes in the Beta 2 band, if there is too much muscle activity (indicating insufficient anesthesia), or if there is low total EEG power in all leads because of burst suppression (too much anesthesia).

What is claimed is:

1. An electroencephalograph (EEG) method using a computer system for controlling anesthesia to a patient undergoing a medical procedure, comprising:
   (a) removably connecting a set of at least two EEG electrodes to the scalp of the patient, at least one EEG electrode at the front of the scalp and at least one other electrode at the back of the scalp, and administering sufficient anesthesia to the patient for the patient to attain the plane of anesthesia selected by an operator;
   (b) amplifying and digitizing the ongoing brain waves of the patient after the patient is anesthetized and before being operated upon and computing power spectrum to provide an initial set of covariance matrices which are self-norm digital data representing a comparison of EEG power in at least one selected frequency band at a frontal EEG electrode with EEG power in the same band at a posterior EEG electrode and recording this initial set of covariance matrices or the average across the set in computer system memory;
   (c) computing the covariance matrix of features extracted from selected EEG electrodes;
   (d) during the operation, digitizing the ongoing brain waves at the same EEG electrodes and extracting the same measures to provide a current set of covariance matrices for the selected measures at the selected EEG electrodes;
   (e) in the computer system, statistically comparing the initial and subsequent sets of univariate digital data and coherence matrices to specify univariate and multivariate distances between the initial set and the current set;
   (f) providing a control signal if the comparison of (e) indicates that the patient is emerging from his fully anesthetized state;
   (g) automatically, in response to the control signal, adjusting the anesthesia administered to the patient during the operation in response to the control signal to restore the patient to the selected plane of anesthesia.

2. The method of claim 1 and automatically, after (a), calculating a system transfer function and defining a correction unit for the individual patient by withholding anesthesia delivery and/or delivering additional anesthetic until the patient's EEG deviates from the self-norm mean value by a selected deviation which is a statistically significant interval.

3. The method of claim 1 and Z-transforming the initial set and current set of covariance matrices using population age-appropriate norms or the self-norm defined by the initial set.

4. The method of claim 1 and including statistically comparing the initial and subsequent sets of data with a normative reference database based on the successful outcomes of specific surgical procedures using specific anesthetic materials.

5. The method of claim 4 in which the normative reference database is in the form of age-corrected Z-scores which thereby transform all measures into the same dimensional units of probability.

6. The method of claim 1 and presenting a set of stimuli to the patient after the patient is anesthetized and both before and during the operation, and amplifying and digitizing the brain wave evoked responses and extracting quantitative descriptors as part of the initial and subsequent sets of digital data.

7. The method of claim 6 wherein the stimuli are auditory and the evoked responses are brain stem or cortical auditory responses (BSER) or auditory 40 Hz Steady State Evoked Potentials (SSEP).

8. The method of claim 6 wherein the stimuli are electrical or tactile and the evoked responses are brainstem or cortical somatosensory evoked responses (BSER).

9. The method of claim 1 wherein measures of the ongoing EEG are derived and recorded, ongoing EEG measures including absolute and relative power in the Delta, Theta, Alpha 1, Alpha 2, Beta 1 and Beta 2 bands, coherence and asymmetry between homologous EEG electrodes, ratios of measures within EEG electrodes or ratios of measures between electrodes, and the spectral edge frequencies below which are found 50% (SEF 50) or 95% (SEF 95) of the total power spectrum.

10. An electroencephalograph (EEG) method using a computer system for controlling anesthesia to a patient undergoing a medical procedure, comprising:

(a) removably connecting a set of at least two EEG electrodes to the scalp of the patient, at least one EEG electrode at the front of the scalp and at least one other electrode at the back of the scalp, and administering sufficient anesthesia to the patient for the patient to attain the plane of anesthesia selected by an operator;

(b) amplifying and digitizing the ongoing brain waves of the patient after the patient is anesthetized and before being operated upon to provide a first set of digital data representing a comparison of EEG power selected from one or more of the Alpha, and/or Theta bands at a frontal EEG electrode with EEG power in the same band at a posterior EEG electrode and recording the first set of digital data in computer system memory;

(c) during the operation, digitizing the ongoing brain waves at the same EEG electrodes and frequency band to provide a second set of digital data representing a co-variance comparison of EEG power in the selected band as between the selected frontal and posterior electrodes;

(d) using the computer system to statistically compare the first and second sets of digital data;

(e) providing a control signal if the comparison of (d) indicates that the patient is emerging from his fully anesthetized state;

(f) automatically, in response to the control signal, adjusting the anesthesia administered to the patient during the operation in response to the control signal to restore the patient to the selected plane of anesthesia.

11. The method of claim 10 and calculating a system transfer function and defining a correction unit for the individual patient by withholding anesthesia delivery and/or delivering extra anesthetic until the patient's EEG deviates from a self-norm mean value by a selected deviation which is a statistically significant interval.

12. The method of claim 10 and including statistically comparing the initial and subsequent sets of data with a normative reference database based on the successful outcomes of specific surgical procedures using specific anesthetic materials.

13. The method of claim 12 in which the normative reference database is in the form of age-corrected Z-scores which thereby transform all measures into the same dimensional units of probability.

14. The method of claim 10 and presenting a set of stimuli to the patient after the patient is anesthetized and both before and during the operation, amplifying and digitizing the brainwave evoked responses and extracting quantitative descriptors of the first and second sets of digital data.

15. The method of claim 14 wherein the stimuli are auditory and the evoked responses are brain stem or cortical auditory responses (BSER) or auditory 40 Hz Steady State Evoked Potentials (SSEP).

16. The method of claim 14 wherein the stimuli are electrical or tactile and the evoked responses are brainstem or cortical somatosensory evoked responses (BSER).

17. The method of claim 10 wherein the measures of the ongoing EEG are derived and recorded and include absolute and relative power in the Delta, Theta, Alpha 1, Alpha 2 and Beta bands, coherence and asymmetry between homologous EEG electrodes, ratios of measures within EEG electrodes or ratios of measures between electrodes, and the spectral edge frequencies below which are found 50% (SEF) or 95% (SEF 95) of the total power spectrum.

18. An electroencephalograph (EEG) method for controlling anesthesia to a patient undergoing a medical procedure, comprising:

(a) removably connecting a set of at least two electrodes to the scalp of the patient, at least one EEG electrode at the front of the scalp and at least one other electrode at the back of the scalp, and administering sufficient anesthesia to the patient for the patient to attain the plane of anesthesia selected by an operator;

(b) providing concurrent sense stimuli in two or more different modes to the patient, the stimuli in one mode being at frequency F1 and the stimuli in the other mode being at a different frequency F2, F3, etc. and amplifying and digitizing the evoked brain waves of the patient after the patient is anesthetized and before being operated upon to provide a first set of F ratio data; and recording the first set of F ratio data in computer system memory;

(c) during the operation repeating the stimulus of (b) and digitizing the evoked brain waves at the same EEG electrodes to provide a second set of F ratio data;

(d) using the computer system to statistically compare the first and second sets of F ratio data;

(e) providing a control signal if the comparison of the F ratio data of (d) indicates that the patient is emerging from his fully anesthetized state; and (f) automatically, in response to the control signal, adjusting the anesthesia administered to the patient during the operation in response to the control signal to restore the patient to the selected plane of anesthesia.

19. A method as in claim 18 wherein the stimulus includes an audio click and a somatosensory skin response voltage or tactile vibration.

20. An electroencephalograph (EEG) system for controlling anesthesia to a patient undergoing a medical procedure, comprising:

(a) a set of at least two EEG electrodes adapted to be removably connected to the scalp of the patient, at least one EEG electrode at the front of the scalp and at least one other electrode at the back of the scalp, and means for administering sufficient anesthesia to the patient for the patient to attain the plane of anesthesia reflected by an operator;

(b) means for amplifying and digitizing the ongoing brain waves of the patient after the patient is anesthetized and before being operated upon to provide an initial set of covariance matrices which are self-norm digital data representing a comparison of EEG power in at least one selected frequency band at a frontal EEG electrode with EEG power in the same band at a posterior EEG electrode and computer system memory means for recording this initial set of covariance matrices;

(c) computer means for computing the covariance matrix of features extracted from selected EEG electrodes;

(d) means for, during the operation, digitizing the ongoing brain waves at the same EEG electrodes and extracting the same measures to provide a current set of covariance matrices for the selected measures at the selected EEG electrodes;

(e) computer means for statistically comparing the initial and subsequent sets of univariate digital data and coherence matrices to specify univariate and multivariate distances between the initial set and the current set;

(f) means for providing a control signal if the comparison of (e) indicates that the patient is emerging from his fully anesthetized state; and (g) means for automatically, in response to the control signal, adjusting the anesthesia administered to the patient during the operation in response to the control signal to restore the patient to the selected plane of anesthesia.

21. The system of claim 20 and means for automatically, after (a), calculating a system transfer function and defining a correction unit for the individual patient by withholding anesthesia delivery or delivering extra anesthetic until the patient's EEG deviates from the self-norm mean value by a selected deviation which is a statistically significant interval.

22. The system of claim 20 and computer means for Z-transforming the initial set and current set of covariance matrices using population age-appropriate norms or the self-norm defined by the initial set.

23. The system of claim 20 and including computer means for statistically comparing the initial and subsequent sets of data with a normative reference database based on the successful outcomes of specific surgical procedures using specific anesthetic materials.

24. The system of claim 23 in which the normative reference database is in the form of age-corrected Z-scores which thereby transform all measures into the same dimensional units of probability.

25. The system of claim 20 and stimuli means for presenting a set of stimuli to the patient before and/or after the patient is anesthetized and both before and during the operation, and means for amplifying and digitizing the brain wave evoked responses and extracting quantitative descriptors as part of the initial and subsequent sets of digital data.

26. The system of claim 25 wherein the stimuli are auditory and the evoked responses are brain stem or cortical auditory responses (BSER) or auditory 40 Hz Steady State Evoked Potentials (SSEP).

27. The system of claim 25 wherein the stimuli are electrical or tactile and the evoked responses are brainstem or cortical somatosensory evoked responses (BSER).

28. The system of claim 20 including means to derive and record ongoing EEG measures including absolute and relative power in the Delta, Theta, Alpha 1, Alpha 2, Beta 1 and Beta 2 bands, coherence and asymmetry between homologous EEG electrodes, ratios of measures within EEG electrodes or ratios of measures between electrodes, and the spectral edge frequencies below which are found 50% (SEF 50) or 95% (SEF 95) of the total power spectrum.

29. An electroencephalograph (EEG) system for controlling anesthesia to a patient undergoing a medical procedure, comprising:

(a) a set of at least two electrodes adapted to be removably connected to the scalp of the patient, at least one EEG electrode at the front of the scalp and at least one other electrode at the back of the scalp, and means for administering sufficient anesthesia to the patient for the patient to attain the plane of anesthesia selected by an operator;

(b) stimuli means for providing concurrent sense stimuli in two or more different modes to the patient, the stimuli in one mode being at frequency F1 and the stimuli in the other mode being at a different frequency F2, F3, etc. and means for amplifying and digitizing the evoked brain waves of the patient after the patient is anesthetized and before being operated upon to provide a first set of F ratio data; and computer means for recording the first set of F ratio data;

(c) means for, during the operation, repeating the stimulus of (b) and digitizing the evoked brain waves at the same EEG electrodes to provide a second set of F ratio data;

(d) computer system means to statistically compare the first and second sets of F ratio data;

(e) means for providing a control signal if the comparison of the F ratio data of (d) indicates that the patient is emerging from his fully anesthetized state; and (f) means for automatically, in response to the control signal, adjusting the anesthesia administered to the patient during the operation in response to the control signal to restore the patient to the selected plane of anesthesia.

30. A system as in claim 29 wherein the stimulus includes an audio click and a somatosensory skin response voltage or tactile vibration.

31. An electroencephalograph (EEG) method using a computer system for controlling anesthesia to a patient undergoing a medical procedure, comprising:

(a) removably connecting a set of at least two EEG electrodes to the scalp of the patient and administering sufficient anesthesia to the patient for the patient to attain the plane of anesthesia selected by an operator;

(b) amplifying and digitizing the brain waves of the patient before and/or after the patient is anesthetized and before being operated upon to provide an initial set of self-norm digital data of selected measures;

(c) during the operation, digitizing the brain waves at the same EEG electrodes and extracting the same measures to provide a current set of data for the selected measures at the selected EEG electrodes;

(d) calculating a system transfer function and defining a correction unit for the individual patient by withholding anesthesia delivery and/or delivering additional anesthetic until variables in the patient's EEG depart from the self-norm mean value by a selected deviation which is a statistically significant interval, and measuring the total amounts of anesthetic required to produce these deviations;

(e) repeating the calculation of (d) at regular intervals during the operation to ascertain possible changes in pharmokinetics;

(f) in the computer system, statistically comparing the initial and subsequent sets of digital data to specify distances between the initial set and the current set;

(g) providing a control signal if the comparison of (f) indicates that the patient is emerging from his plane of anesthesia;

(h) automatically, in response to the control signal, adjusting the anesthetic administered to the patient during the operation in response to the control signal, in an amount determined by the transfer function of (d), to restore the patient to the selected plane of anesthesia.

* * * * *